United States Patent [19]

Holt et al.

[11] 4,229,347

[45] Oct. 21, 1980

[54] LIQUID DIPHENYLMETHANE DIISOCYANATE COMPOSITIONS

[75] Inventors: John B. Holt; Arthur Ibbotson, both of Manchester, England

[73] Assignee: Imperial Chemical Industries Limited, London, England

[21] Appl. No.: 24,774

[22] Filed: Mar. 28, 1979

[30] Foreign Application Priority Data

Apr. 11, 1978 [GB] United Kingdom ............... 14130/78

[51] Int. Cl.$^2$ ................. C07C 119/048; C07D 229/00
[52] U.S. Cl. ......................... 260/239 A; 260/453 AM; 260/453 SP
[58] Field of Search ................. 260/453 AM, 453 SP, 260/239 A, 239 R

[56] References Cited

U.S. PATENT DOCUMENTS

| | | |
|---|---|---|
| 3,394,164 | 7/1968 | McClellan et al. ............ 260/453 SP |
| 3,644,457 | 2/1972 | Ronig et al. ................... 260/453 SP |
| 3,883,571 | 5/1975 | Allport et al. ................ 260/453 AM |
| 4,031,026 | 6/1977 | Ibbotson .................. 260/453 AM X |
| 4,118,411 | 10/1978 | Reiff et al. ..................... 260/453 SP |

Primary Examiner—Dolph H. Torrence
Attorney, Agent, or Firm—Cushman, Darby & Cushman

[57] ABSTRACT

A liquid diphenylmethane diisocyanate composition which comprises diphenylmethane diisocyanate in which from 10 to 35% of the isocyanate groups have been reacted with a mixture of alkylene glycols each containing at least three carbon atoms, one of the glycols being dipropylene glycol, tripropylene glycol or a higher propylene glycol. The composition is made by heating together the reactants.

14 Claims, No Drawings

LIQUID DIPHENYLMETHANE DIISOCYANATE COMPOSITIONS

This invention relates to liquid isocyanate compositions based on diphenylmethane diisocyanate and to the manufacture of such compositions.

Diphenylmethane diisocyanate is a solid isocyanate available on the commercial scale and as available, normally consists largely of the 4,4'-isomer with a small content of the 2,4'-isomer. The two isomers are both solids at room temperature having melting points of 42° C. and 36° C. respectively, commercial mixtures of the two isomers optionally containing other isomers such as the 2,2'-isomer in small quantities are also solid at room temperature.

One of the end-uses for diphenylmethane diisocyanate is in the manufacture of micro-cellular plastics for example for use in shoe soles. The micro-cellular plastics may be made by reacting the diisocyanate with a polyester or polyether and a cross-linking agent or chain extender under such conditions that a small amount of gas is generated to form a micro-cellular product. In order that it may be incorporated at room temperature into the polyester or polyether it is preferred that the diisocyanate to be used be in the liquid state at room temperature.

Liquid diphenylmethane diisocyanate compositions are also useful for other end-uses where it is desirable that the diisocyanate be in the liquid form.

Our British Pat. No. 1378975 describes and claims liquid diphenylmethane diisocyanate compositions which comprise diphenylmethane diisocyanate in which from 10% to 30% of the isocyanate groups have been reacted with a mixture of alkylene glycols containing at least three constituent glycols each having at least three carbon atoms.

We have now found that particularly valuable compositions which have good resistance to crystallisation are obtained when one of the constituent glycols is dipropylene glycol, tripropylene glycol or a polypropylene glycol.

Thus, according to the present invention there is provided an improvement in or modification of the invention claimed in Claim 1 of British Pat. No. 1378975 which comprises a liquid diphenylmethane diisocyanate composition comprising a diphenylmethane diisocyanate in which from 10% to 35% of the isocyanate groups have been reacted with a mixture of alkylene glycols containing at least three constituent glycols each having at least three carbon atoms, one of said glycols being dipropylene glycol, tripropylene glycol or a higher polypropylene glycol.

Any solid diphenylmethane diisocyanate may be used in making the compositions of the present invention including for example diphenylmethane-4,4'-diisocyanate, diphenylmethane-2,4'-diisocyanate and mixtures of these, optionally containing small amounts of other isomers. Substantially pure diphenylmethane-4,4'-diisocyanate may be used, for example diphenylmethane-4,4'-diisocyanate containing not more than 10% by weight of isomers thereof. We have found, however that improved liquidity of the composition may be obtained using diphenylmethane-4,4'-diisocyanate containing up to 5% by weight of diphenylmethane-2,4'-diisocyanate.

One of the alkylene glycols with which the isocyanate groups of the diphenylmethane diisocyanate have been reacted must be either dipropylene glycol, tripropylene glycol or a higher polypropylene glycol. The higher polypropylene glycols are generally made by addition of propylene oxide to propylene glycol and consist of a mixture of polypropylene glycols of varying molecular weight; they are normally defined by their number average molecular weight. The term a higher polypropylene glycol used in this specification includes such mixed polypropylene glycols.

Examples of alkylene glycols which may be used as constituents of the alkylene glycol mixture include diethylene glycol, triethylene glycol, tetraethylene glycol, 1,2- and 1,3-propylene glycols, neopentyl glycol, 1,3-butylene glycol and 1,2-butylene glycol.

The proportions of the three or more glycols contained in the mixture may vary widely, and in part the proportions will be dependent on the particular glycols used. Although proportions outside this range may be used we have found that convenient mixtures of glycols are those wherein the molar percentage of any one of the glycols is not more than 70% and not less than 15% of total glycols used. We prefer compositions wherein the molar percentage of any one of the glycols is not more than 50% and not less than 25% of the total glycols used. Where more than three glycols are used, the constituents of the alkylene glycol mixture are preferably selected such that no more than two of the glycols are other than dipropylene glycol, tripropylene glycol or a higher propylene glycol.

Preferred mixtures of glycols are mixtures of dipropylene glycol or tripropylene glycol with two other alkylene glycols each of which has at least one secondary hydroxyl group. It is preferred that in such mixtures the dipropylene glycol or the tripropylene glycol is present in an amount of 27–45 molar percent, for example 27–31 molar percent of the total glycols and that the two other alkylene glycols are in approximately equal molar proportions.

In order to obtain compositions in which from 10% to 35% of the isocyanate groups have been reacted with the alkylene glycol mixture, 1 molar proportion of the diphenylmethane diisocyanate is reacted with from 0.1 to 0.35 molar proportions of the alkylene glycol mixture. We prefer to use from 0.15 to 0.30 molar proportions of the alkylene glycol mixture, which results in reaction of 15% to 30% of the isocyanate group. The molar proportions of alkylene glycol mixture referred to above is the sum total of the molar proportions of the alkylene glycol constituents of the mixture.

The compositions of the invention are made by mixing together the diphenylmethane diisocyanate and the mixed alkylene glycols and reacting. The reaction is conveniently carried out at a temperature of 40° to 120° C. preferably 60° to 100° C. although temperatures outside the wider range may be used. A convenient method of performing the mixing and reaction is to melt the diisocyanate, to add the mixed alkylene glycols dropwise thereto and then heat until reaction is complete. Alternatively the glycols may be added separately in any order to the diisocyanate.

The final product may then be cooled to room temperature and remains liquid at that temperature on storage.

Optionally stabilisers for example, benzoyl chloride, adipic acid, phosphoric acid or antioxidant may be added before, during or after the reaction.

The product is useful as a liquid isocyanate for the manufacture of polyurethanes and is particularly useful for the manufacture of microcellular polyurethane.

We use the term liquid in relation to the diphenylmethane diisocyanate compositions described herein to indicate that compositions remain liquid at room temperature for long periods of time, sufficient in fact for all practical purposes. We do not however claim that the compositions would remain liquid if stored at room temperature for several years as we believe the effect of introducing the alkylene glycol mixture into the molecule is one of retarding the rate of crystallisation rather than one of lowering the melting point to below room temperature. Nevertheless for all practical purposes the compositions may be considered as liquids.

There may be incorporated in the diphenylmethane diisocyanate composition (either before, during or after the reaction with the mixture of alkylene glycols) up to 1.5% by weight based on diphenylmethane diisocyanate of higher homologues of diphenylmethane diisocyanate such as are produced, for example, during the manufacture of diphenylmethane diisocyanate by the phosgenation of the reaction product of aniline and formaldehyde. There may also be advantageously incorporated in the diphenylmethane diisocyanate composition a proportion of diphenylmethane diisocyanate whose liquidity has been modified by other agents. For example diphenylmethane-4,4'-diisocyanate may be introduced into the composition (either before, after or during the reaction with the mixture of alkylene glycols) which has been modified as described in British Pat. No. 1476088 by the formation of a uretonimine derivative. Preferably the concentration of uretonimine derivatives in the composition of the present invention does not exceed 2.5% by weight based on total diphenylmethane-4,4'-diisocyanate. If the diphenylmethane diisocyanate composition contains both higher homologues of diphenylmethane diisocyanate and a uretonimine derivative of diphenylmethane-4,4'-diisocyanate, the total concentration of higher homologues and uretonimine derivative preferably does not exceed 2% by weight based on total diphenylmethane diisocyanate.

The invention is illustrated by the following Examples in which all parts are by weight except where otherwise stated.

EXAMPLE 1

58.8 Parts of an equimolecular mixture of 1,2-propylene glycol, 1,3-butylene glycol and dipropylene glycol of water content below 0.05% was added to 600 parts of molten diphenylmethane-4,4'-diisocyanate, in which 0.18 parts of benzoyl chloride had been dissolved, and stirred for 80° C. for 2 hours. The product had isocyanate content 23.1% and viscosity at 25° C., 11.1 stokes. The results of storage at various temperatures are given in Table 1.

In a comparative experiment in which 54.4 parts of an equimolecular mixture of 1,2-propylene glycol, 1,3-butylene glycol and diethylene glycol were reacted under identical conditions with the same diisocyanate the product had isocyanate content 23.1% and viscosity at 25° C., 12.8 stokes.

EXAMPLE 2

58.25 Parts of a mixture of 1 molar proportion of 1,2-propylene glycol, 1 molar proportion of 1,3-butylene glycol and 0.9 molar proportions of dipropylene glycol was reacted as in Example 1 with 600 parts of diphenylmethane-4,4'-diisocyanate. The product had isocyanate content 23.1% and viscosity at 25° C., 12.7 stokes.

In a comparative example in which 54.2 parts of a mixture of 1 molar proportion of 1,2-propylene glycol, 1 molar proportion of 1,3-butylene glycol and 0.9 molar proportions of diethylene glycol were reacted with 600 parts of diphenylmethane-4,4'-diisocyanate the product had isocyanate content 23.1% and viscosity at 25° C., 14.8 stokes.

The results of storage at various temperatures are outlined in Table 1.

EXAMPLE 3

67.35 Parts of a mixture of 1 molar proportion of 1,2-propylene glycol, 1 molar proportion of 1,3-butylene glycol and 1 molar proportion of tripropylene glycol was reacted as in Example 1 with 600 parts of diphenylmethane-4,4'-diisocyanate. The product had isocyanate content 23.1% and viscosity at 25° C., 8.4 stokes.

TABLE 1

| | Storage Temperature 13–15° C. | | Storage Temperature 8–10° C. |
|---|---|---|---|
| | Time (in days) for crystallisation to start | Amount of crystallisation be 50% complete after 62 days | Amount of crystals after 3 days |
| Example 1 | 9 | 42 | 95% | 90% |
| Example 1 (Comparative) | 2 | 34 | 100% | 95% |
| Example 2 | >62 | >62 | 0 | 40% |
| Example 2 (Comparative) | 15 | 38 | 85% | 85% |
| Example 3 | 49 | >62 | 10% | 85% |

EXAMPLE 4

6.31 parts of a mixture of 1 molar proportion of 1,2-propylene glycol, 1 molar proportion of 1,3-butylene glycol and 0.9 molar proportion of dipropylene glycol was reacted in the presence of 0.015% (based on total diphenylmethane diisocyanate) of benzoyl chloride, as in Example 1, with 52.34 parts of diphenylmethane-4,4'-diisocyanate and 14.76 parts of a mixture consisting of 8.8% diphenylmethane-2,4'-diisocyanate and 91.2% diphenylmethane-4,4'-diisocyanate. The product had an isocyanate content of 23.27% and a viscosity at 25° C. of 10.7 poise.

The results of storage tests are given in Table 2.

EXAMPLE 5

100 parts of the product of Example 4 were stirred at 50° C. for 45 minutes with 5 parts of a polyisocyanate composition (referred to hereinafter as modified MDI) consisting of diphenylmethane-4,4'-diisocyanate modified as described in United Kingdom Pat. No. 1476088 by the formation of a uretonimine derivative and having an isocyanate content of 29.5%. The resulting composition had an isocyanate content of 23.67% and a viscosity at 25° C. of 8.9 poise.

The results of storage tests for the composition of Example 5 are given in Table 2.

EXAMPLE 6

The procedure of Example 4 was repeated replacing the dipropylene glycol with tripropylene glycol.

Thus 7.30 parts of a mixture of 1 molar proportion of 1,2-propylene glycol, 1 molar proportion of 1,3-butylene glycol and 1 molar proportion of tripropylene glycol was reacted in the presence of benzoyl chloride with 51.97 parts of diphenylmethane-4,4'-diisocyanate and 14.67 parts of a mixture consisting of 8.8% diphenylmethane-2,4'-diisocyanate and 91.2% diphenylmethane-4,4'-diisocyanate. The product had an isocyanate content of 23.09% and a viscosity at 25° C. of 10.7 poise.

The results of storage tests are given in Table 2.

EXAMPLE 7

100 parts of the product of Example 6 were stirred at 50° C. for 45 minutes with 5 parts of "Modified MDI". The resulting composition had an isocyanate content of 23.48% and a viscosity at 25° C. of 8.8 poise.

The results of storage tests for the composition of Example 7 are given in Table 2.

EXAMPLE 8

7.30 parts of a mixture of 1 molar proportion of 1,2-propylene glycol, 1 molar proportion of 1,3-butylene glycol and 0.9 molar proportion of tripropylene glycol was reacted in the presence of benzoyl chloride, as in Example 1, with 65.74 parts of diphenylmethane-4,4'-diisocyanate. The product had an isocyanate content of 22.92% and a viscosity at 25° C. of 11.3 poise.

The results of storage tests are given in Table 2.

In a comparative experiment using 5.87 parts of a corresponding mixture of diols consisting of 1 molar proportion of 1,2-propylene glycol, 1 molar proportion of 1,3-butylene glycol and 0.9 molar proportion of diethylene glycol, the product had an isocyanate content of 23.13 poise and a viscosity at 25° C. of 14.2 poise.

The results of storage tests for the comparative composition are given in Table 2.

EXAMPLE 9

100 parts of the product of Example 8 were stirred at 50° C. for 45 minutes with 5 parts of "Modified MDI". The resulting composition had an isocyanate content of 23.17% and a viscosity at 25° C. of 8.3 poise.

By way of comparison, the comparative product described in Example 8 was similarly stirred with "Modified MDI" and the resulting composition had an isocyanate content of 23.46% and a viscosity at 25° C. of 11.0 poise.

The results of storage tests for the composition of Example 9, and the comparative composition described above are given in Table 2.

TABLE 2

| Example No. | Storage at 14 to 16° C. | | Storage at 10 to 12° C. | |
|---|---|---|---|---|
| | No. of days | % solids | No. of days | % solids |
| 4 | 50 | less than 1 | 48 | 100 |
| | 97 | less than 1 | | |
| 5 | 50 | 0 (clear liquid) | 70 | 10 |
| | 97 | 0 (clear liquid) | | |
| 6 | 50 | 0 (clear liquid) | 70 | 90 |
| | 97 | 0 (clear liquid) | | |
| 7 | 50 | 0 (hazy liquid) | 70 | 10 |
| | 97 | 0 (hazy liquid) | | |
| 8 | 50 | 35 | 22 | 100 |
| | 97 | 40 | | |
| 8 (comparison) | 50 | 75 | 2 | 100 |
| | 97 | 90 | | |
| 9 | 50 | 0 (clear liquid) | 70 | 30 |
| | 97 | 0 (hazy liquid) | | |
| 9 (comparison) | 50 | less than 1 | 48 | 100 |
| | 97 | about 1 | | |

EXAMPLE 10

3.98 parts of a mixture of 1 molar proportion of 1,2-propylene glycol, 1 molar proportion of 1,3-butylene glycol and 0.9 molar proportion of dipropylene glycol was reacted in the presence of benzoyl chloride, as in Example 1, with 41.02 parts of diphenylmethane-4,4'-diisocyanate, except that in this Example there was incorporated in the reaction mixture 5.0 parts of "Modified MDI". The product had an isocyanate content of 23.79% and a viscosity at 25° C. of 7.5 poise.

The results of storage tests for the composition of Example 10 are given in Table 3.

TABLE 3

Storage at 4 to 50° C.
Time (days) to reach a degree of crystallisation of:

| 10% | 50% | 100% |
|---|---|---|
| 10 | 16 | 33 |

Storage at 13 to 16° C.
Slight haze after 101 days.

We claim:

1. A liquid diphenylmethane diisocyanate composition comprising diphenylmethane-4,4'-diisocyanate containing not more than 10% by weight of isomers thereof in which from 10% to 35% of the isocyanate groups have been reacted with a mixture of alkylene glycols containing at least three constituent glycols each having at least three carbon atoms, one of said glycols being dipropylene glycol, tripropylene glycol or a higher polypropylene glycol.

2. A composition according to claim 1 wherein the diphenylmethane diisocyanate is diphenyl-4,4'-diisocyanate containing up to 5% by weight of diphenylmethane-2,4'-diisocyanate.

3. A composition according to claim 1 wherein the constituent glycols of the mixture of alkylene glycols are present in such proportion that the molar percentage of any one of the glycols is not more than 70% and not less than 15% of the total glycols used.

4. A composition according to claim 3 wherein the molar percentage of any one of the glycols is not more than 50% and not less than 25% of the total glycols used.

5. A composition according to claim 1 wherein the mixture of alkylene glycols is a mixture of dipropylene glycol or tripropylene glycol with two other alkylene glycols each of which has at least one secondary hydroxyl group.

6. A composition according to claim 5 wherein the dipropylene glycol or the tripropylene glycol is present in an amount of from 27 to 31 molar percent of the total glycols and the two other alkylene glycols are in approximately equal molar proportions.

7. A composition according to claim 5 wherein the dipropylene glycol or the tripropylene glycol is present in an amount from 27 to 45 molar percent of the total glycols and the two other alkylene glycols are in approximately equal molar proportions.

8. A composition according to claim 1 wherein the mixture of alkylene glycols contains 1,2-propylene glycol or 1,3-butylene glycol.

9. A composition according to claim 1 wherein from 15% to 30% of the isocyanate groups have been reacted.

10. A composition according to claim 1 which additionally contains diphenylmethane-4,4'-diisocyanate which has been modified by the formation of a uretonimine derivative.

11. A process for the manufacture of a composition according to claim 1 which comprises heating together diphenylmethane diisocyanate with a mixture of alkylene glycols containing at least three constituent glycols each having at least three carbon atoms, one of said glycols being dipropylene glycol, tripropylene glycol or a higher propylene glycol.

12. A process according to claim 11 wherein the heating is carried out at a temperature of from 40° to 120° C.

13. A process according to claim 12 when the heating is carried out at a temperature of from 60° to 100° C.

14. A process according to claim 11 wherein there is incorporated in the reaction mixture a diphenylmethane-4,4'-diisocyanate which has been modified by the formation of a uretonimine derivative.

* * * * *